United States Patent [19]

McLeod et al.

[11] Patent Number: 5,765,229
[45] Date of Patent: Jun. 16, 1998

[54] SUN VISOR CAP HEADGEAR FOR USE DURING WATER ACTIVITIES

[76] Inventors: Jody E. McLeod, 7205 Olivetas Ave.; Brock J. Rosenthal, 7709 Prospect Pl., both of La Jolla, Calif. 92037

[21] Appl. No.: 720,419

[22] Filed: Sep. 30, 1996

[51] Int. Cl.⁶ .................................................. A42B 1/06
[52] U.S. Cl. .................. 2/195.1; 2/172; 2/181; 2/181.2; 2/195.3; 2/200.1; 2/200.2; 2/423; 2/68
[58] Field of Search .................. 2/172, 195.1, 423, 2/12, 175.1, 175.6, 175.7, 181, 181.2, 181.4, 195.3, 200.1, 200.2, 421, 68

[56] References Cited

U.S. PATENT DOCUMENTS

| | | | |
|---|---|---|---|
| 1,598,314 | 8/1926 | Rosenberg | 2/195.1 |
| 2,769,308 | 11/1956 | Krasno | 2/12 |
| 3,979,777 | 9/1976 | Gregg | 2/68 |
| 4,768,231 | 9/1988 | Schrack | 2/68 |
| 5,046,193 | 9/1991 | Foresman et al. | 2/68 |
| 5,099,524 | 3/1992 | Linday | 2/195.1 |
| 5,351,343 | 10/1994 | Harbison | 2/172 |

*Primary Examiner*—Diana Biefeld
*Attorney, Agent, or Firm*—Flanagan & Flanagan; John R. Flanagan; John K. Flanagan

[57] ABSTRACT

A sun visor headgear includes a band for fitting around the head of a wearer and defining an opening for receiving the top of the head of the wearer, a front bill connected to the band and extending outwardly and downwardly therefrom for shielding the face of the wearer, and a chin strap attached to opposite side portions of the band rearwardly of the front bill and defining a loop for extending over the ears and under the chin of the wearer. The band and front bill are made integral with one another in a one-piece structure or, alternatively, the band can be a separate linear strip attached to the front bill. The band has a pair of rear edge portions defining the only location at it is attached to itself. The chin strap is made from a blank having a bow tie shaped configuration with opposite end portions attached to inner opposite portions of an upper edge of the band and interconnected by a middle portion. The opposite end portions taper from a maximum width for covering the wearer's ears to a minimum width of the middle portion for extending under the wearer's chin. A combined sun visor and cap headgear has a cap piece with a folded lower edge portion receiving and enclosing the band and opposite ends of the chin strip attached to the folded lower edge portion of the cap piece rearwardly of the front bill.

8 Claims, 3 Drawing Sheets

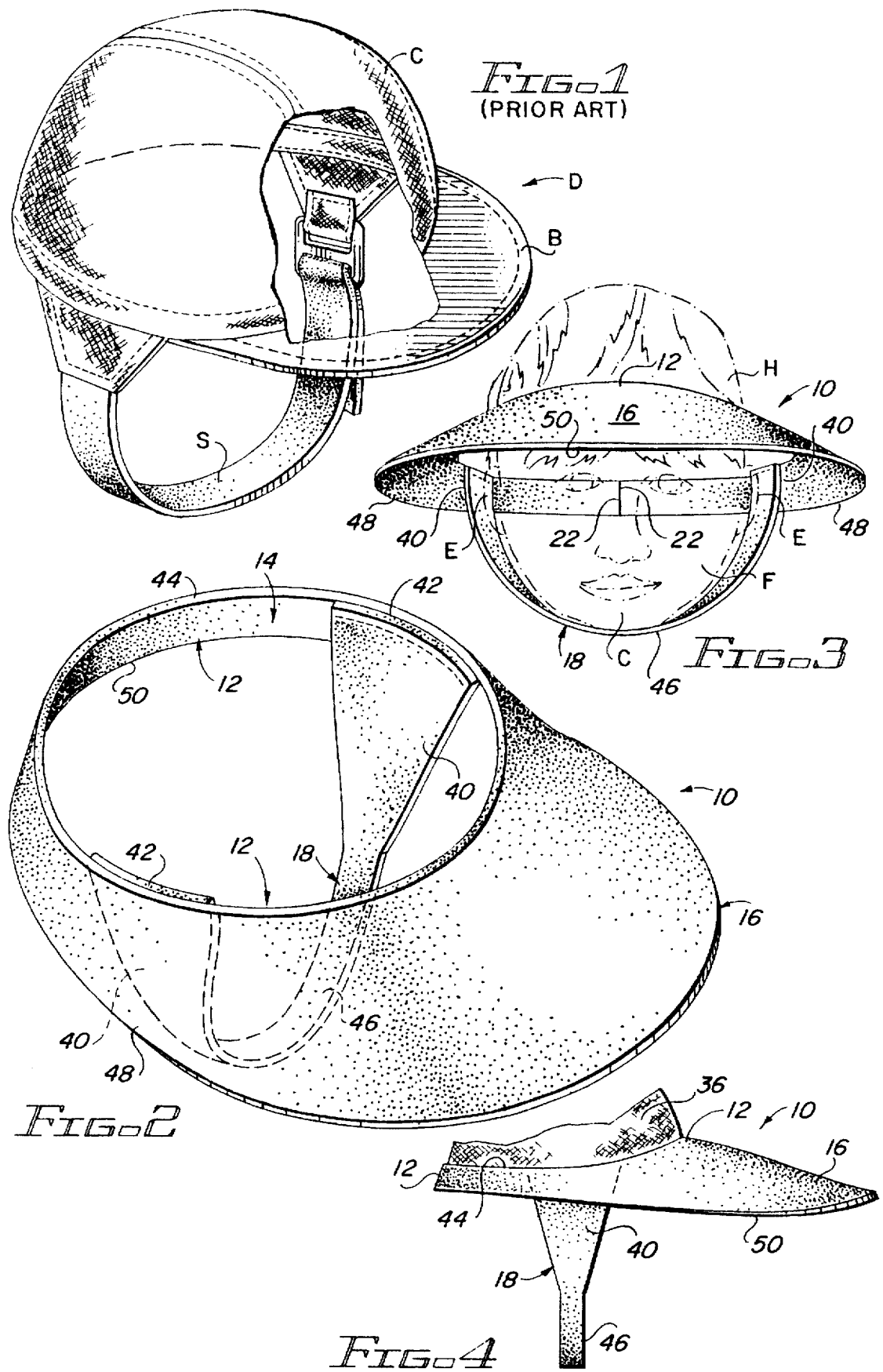

SUN VISOR CAP HEADGEAR FOR USE DURING WATER ACTIVITIES

BACKGROUND OF THE INVENTION

1. Field of the Invention

The present invention generally relates to headgear or outdoor activities and, more particularly, is concerned with sun visor and cap headgear for protecting a wearer's face from harmful sun rays exposure and a wearer's ears from harmful sun, wind and water exposure.

2. Description of the Prior Art

The general public has become increasingly concerned about damage to their body from the sun. Those involved in outdoor water activities such as boating and surfing have difficulty protecting their faces from harmful exposure to the sun's rays and their ears from harmful exposure to the wind and water. When in or around water, people sometimes wear caps or visors designed for terrestrial activities such as baseball or golf or they use one of a few articles designed especially for water activities.

A problem exists, however, with using those caps or visors made for terrestrial activities in that the cap or visor provides no protection for the wearer's ears and may fall off if a wearer is submerged under water and thus fail to continuously protect the wearer's face. While this may not be a problem on land, a lost cap or visor in the water may never be seen again. As a result of this apparent inadequacy of caps and visors made for land activities, a few articles have been developed over the years specifically designed for use during activities in water. Representative examples of these articles are disclosed in U.S. Pat. No. 3,979,777 to Gregg, U.S. Pat. No. 4,768,231 to Schrack and U.S. Pat. No. 5,046,193 to Foresman et al. Of these examples, only the article disclosed in the patent to Schrack attempts to provide protection from the sun for the wearer's face while the articles disclosed in the other two patents attempt to provide protection from the wind and water for the wearer's ears.

The articles of the Gregg and Foresman et al patents snugly cover the head and ears and not the face. These articles would be too hot and uncomfortable to wear for an extended period of time while the wearer is out of the water. The article of the Schrack patent and other like caps and visors have bills which are either too rigid creating too much hydrodynamic drag when submerged in water causing either loss of the headgear or excessive strain to the wearer's head from the force of the water acting against the bill or are too small and appear not to provide adequate sun protection. Also, as in the case of the article of the Schrack patent, many of the devices in the prior art appear not to have a means for adequately securing the cap or visor to the head so as to prevent the cap or visor from being forced off the head upon the wearer being submerged in water.

Consequently, a need still exists for headgear which overcomes the aforementioned problems with prior art articles and will provide face and ear protection without substituting new problems in the place of the current problems that are eliminated.

SUMMARY OF THE INVENTION

The present invention provides a sun visor and cap headgear designed to satisfy the aforementioned need. The sun visor and cap headgear of the present invention provides a bill which is large enough to block harmful sun rays from a wearer's face and which is made of a material which is not rigid enough to cause a significant hydrodynamic drag problem. The headgear also provides a chin strap to cover the wearer's ears. The headgear further can have a cap piece to provide coverage of the portion of the wearer's head extending through an opening defined by the band.

Accordingly, the present invention is directed to a sun visor headgear for use primarily during activities in the water but not so limited thereto. The sun visor headgear comprises: (a) a band for fitting continuously around and surrounding the head of a wearer and defining an opening therethrough for exposing the top of the head of the wearer; (b) a front bill connected to the band and extending outwardly and downwardly therefrom for shielding the face of the wearer; and (c) a chin strap attached to opposite side portions of the band rearwardly of the front bill and defining a loop therebetween for extending over the ears and under the chin of the wearer.

More particularly, the band and the front bill are made integral with one another in a one-piece structure fabricated from a first blank of material having a horsecollar shaped configuration. In one embodiment, the first blank fabricated from a substantially uniform elastic bendable material, such as closed cell neoprene rubber, which makes the front bill compliant enough to eliminate the problem of hydrodynamic drag and yet is rigid enough to support itself so it can extend out from the continuous band without requiring reinforcement. In another embodiment, the first blank is fabricated from a plastic foam type of material that is bendable but substantially inelastic.

Also, the first blank which forms the band has a pair of rear edge portions defining the only location at which the first blank is attached to itself to form the band and the bill. The attachment can be permanent or by use of releasable fastening elements, such as hook and loop fasteners, snaps, etc.

The chin strap is fabricated from a second blank of material having a bow tie shaped configuration. The second blank is also comprised of a substantially uniform elastic bendable material, such as closed cell neoprene rubber. The second blank particularly has opposite end portions attached at opposite end edges thereof along inner opposite portions of an upper edge of the band defining the opening therein. The opposite end portions of the second blank are tapered from a maximum width at the opposite end edges thereof for covering the ears of the wearer to a minimum width at a middle portion for extending under the chin of the wearer. The opposite end edges of the second blank are preferably attached to the inner opposite portions of the band so as not to interfere with the bill in the ear areas. This interior location of attachment of the opposite end edges of the second blank forming the ear covers and the chin strap to the inner opposite portions of the band enables the front bill to provide more shade when the sun is at one side rather than directly ahead of the wearer.

A cap piece may also be attached to the band to enclose the opening therein and to cover the head of the wearer. The chin strap can be easily tucked into the cap piece during non-use so that the device can be comfortable to wear when the wearer is not on or in the water.

The present invention is also directed to a combined sun visor and cap headgear for use primarily during activities in the water but not so limited thereto. For example, the headgear is useful in other applications where a helmet is worn, such as cycling, kayaking or white water rafting. For helmet applications the visor is sized accordingly to fit over the helmet. The combined sun visor and cap headgear comprises: (a) a band for fitting continuously around and surrounding the head of a wearer and defining an opening therethrough for receiving the top of the head of the wearer; (b) a front bill connected to the band and extending outwardly and downwardly therefrom for shielding the face of the wearer; (c) a cap piece attached to the band to enclose the opening therein and to cover the head of the wearer; and (d) a chin strap attached to one of the opposite side portions of the cap piece and of the band rearwardly of the front bill and defining a loop therebetween for extending over the ears and under the chin of the wearer. As an example, the cap piece can have a folded lower edge portion defining an enclosed channel receiving and enclosing the band. Opposite ends of the chin strip can be attached to the folded lower edge portion of the cap piece rearwardly of the front bill. Other means of attachment can equally be utilized.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a top perspective view of a prior art headgear of the present invention showing a portion broken away.

FIG. 2 is a top perspective view of one embodiment of the present invention being a sun visor headgear.

FIG. 3 is a reduced front perspective view of the headgear.

FIG. 4 is a side elevational view of the headgear of FIG. 3.

DETAILED DESCRIPTION OF THE INVENTION

Figure 5:
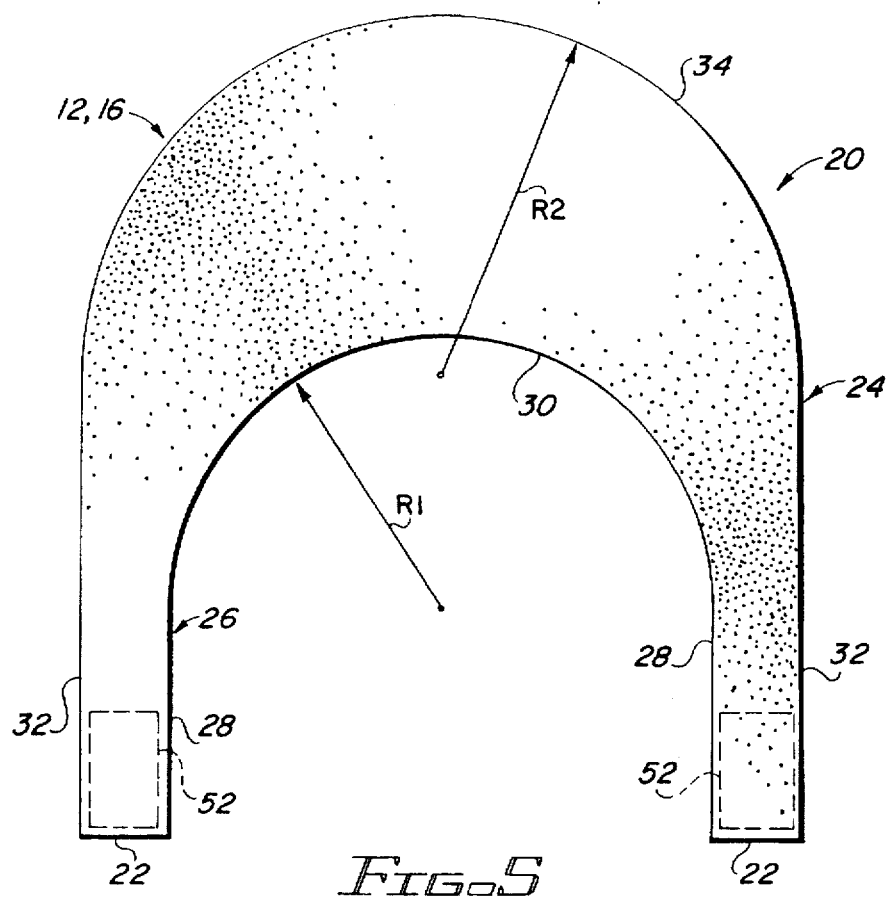
FIG. 5 is a top plan view of a first blank of material having a horsecollar shaped configuration for forming a band and front bill of the headgear.

Referring to the drawings and particularly to FIGS. 2 to 4, there is illustrated one embodiment of the present invention in the form of a sun visor headgear, generally designated 10, for use particularly, although not solely, during water activities to protect a wearer's face F from harmful sun rays and wearer's ears E from harmful wind and water. The headgear 10 functions by providing a profile that creates a shadow large enough to block sun rays from the wearer's face F while being made of a material which is not rigid enough to cause a significant hydrodynamic drag problem.

The headgear 10 incorporates features which overcome drawbacks of the prior art described earlier in the background and such as exemplified by the prior art headgear shown in FIG. 1. The prior art headgear D generally includes a top cap C having a front bill B with an adjustable chin strap S. The front bill B is generally too rigid for water activities involving frequent submergence under water or is too small to adequately protect the wearer's face from the sun.

Referring still to FIGS. 2-4, the sun visor headgear 10 basically includes a band 12 for fitting continuously around and surrounding the head H of a wearer and defining an opening 14 therethrough for exposing the top of the head of the wearer, a front bill 16 connected to the band 12 and extending outwardly and downwardly therefrom for shielding the face F of the wearer, and a chin strap 18 attached to opposite side portions of the band 12 rearwardly of the bill 16 and defining a loop therebetween for extending over the ears E and under the chin C of the wearer.

Figure 7:
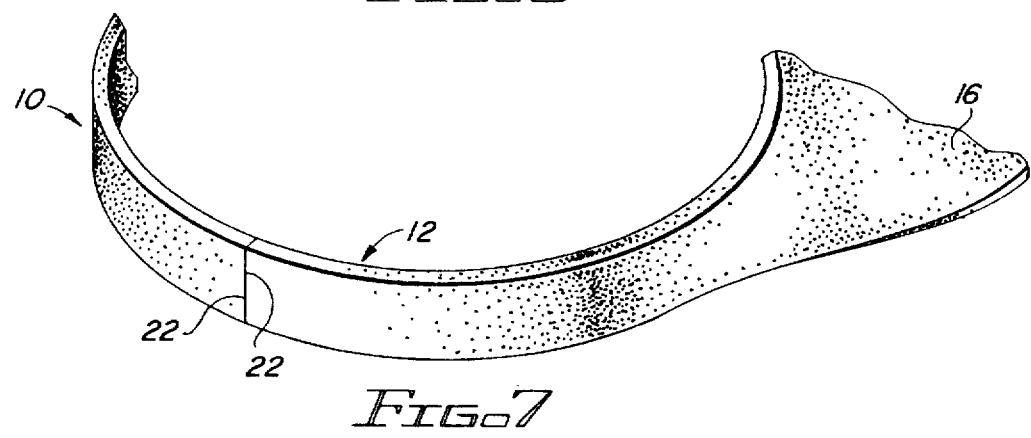
FIG. 7 is a fragmentary rear perspective view of the first blank formed into the band of the headgear.
Figure 8:
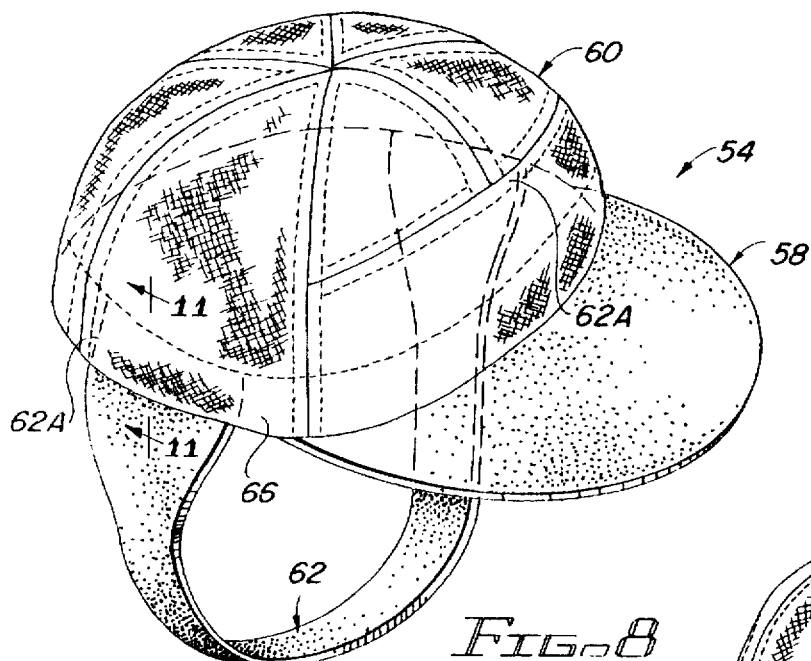
FIG. 8 is a top perspective view of another embodiment of the present invention being a combined sun visor and cap headgear.
Figure 10:
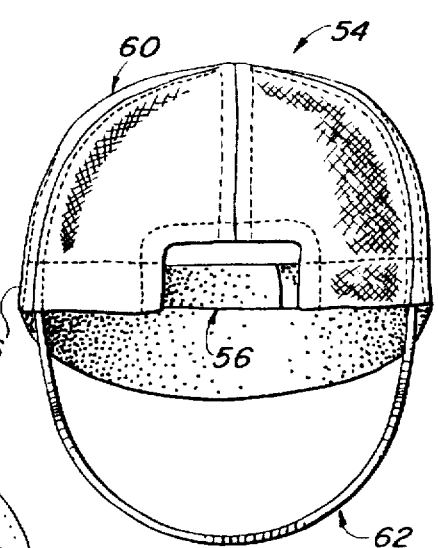
FIG. 10 is rear elevational view of the headgear of FIG. 8.

Referring also to FIGS. 5 and 7, the band 12 and the front bill 16 of the headgear 10 are preferably made integral with one another in a one-piece structure fabricated from a first blank 20 of material generally having a horsecollar shaped configuration. In one embodiment, the first blank 20 is fabricated from a substantially uniform elastic bendable material, for example a closed cell neoprene rubber, which is compliant enough to eliminate the hydrodynamic drag problem and yet is rigid enough to support itself so it can extend out from the continuous band 12 without requiring reinforcement. For instance, the neoprene rubber of the first blank 20 is generally from 5 mm to 9 mm thick which allows the bill 16 to be constructed with sufficient stiffness and large enough so that the entire face and parts of the chest of the wearer are shaded. The curvature of the bill 16 imparted by the design of the device 10 adds to its stiffness without adding any supporting structure. The neoprene also provides additional benefits of being waterproof, easily wrung dry, floatable and lightweight. In another embodiment, the first blank 20 can be fabricated from a plastic foam type of material that is bendable but substantially inelastic.

The first blank 20 particularly has a pair of rear edge portions 22 defining the only location at which the first blank 20 is attached to itself to form the band 12 and the bill 16. The first blank 20 has a generally U-shaped outer periphery 24 and a generally U-shaped inner periphery 26 spaced inwardly from the U-shaped outer periphery 24. The U-shaped inner periphery 26 has a pair of substantially parallel inner straight portions 28 and a curved inner bight portion 30 interconnecting the inner straight portions 28. The U-shaped outer periphery 24 has a pair of substantially parallel outer straight portions 32 and a curved outer bight portion 34 interconnecting the outer straight portions 32. The inner straight portions 28 of the U-shaped inner periphery 26 are shorter in length than the outer straight portions 32 of the U-shaped outer periphery 24. Also, the curved inner bight portion 30 of the U-shaped inner periphery 26 has a radius R1 that is shorter than the radius R2 of the curved outer bight portion 34 of the U-shaped outer periphery 24. The bill 16 further has a substantially greater area than the band 12.

Referring to FIG. 4, in an additional embodiment of the present invention, the sun visor headgear 10 can also include a cap piece 36. In this embodiment, the cap piece 36 is attached to the band 12 to extend thereabove and enclose the opening 14 therein and to cover the head of the wearer. The cap piece 36 can be made of any suitable lightweight, waterproof fabric such as Nylon or Lycra, or neoprene for colder environments.

Figure 6:
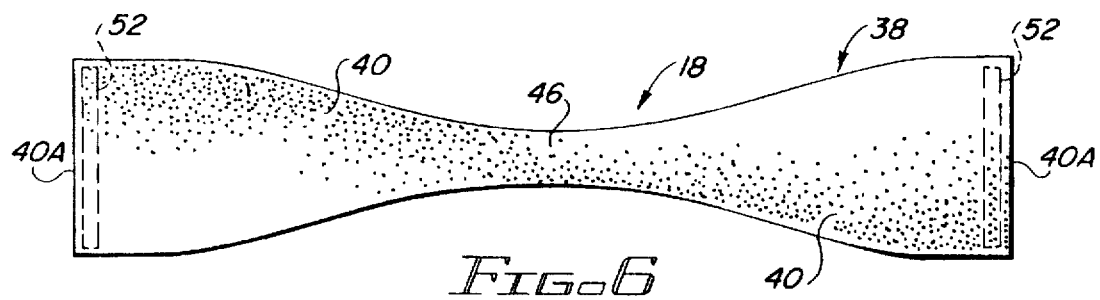
FIG. 6 is a top plan view of a second blank of material having a bow tie shaped configuration for forming the ear covers and chin strap of the headgear.

Referring to FIG. 6, the chin strap 18 of the sun visor headgear 10 is fabricated from a second blank 38 of material having a bow tie shaped configuration. The second blank 38 may be composed of a substantially uniform elastic bendable material, for example the closed cell neoprene rubber, which is from 1 mm to 2 mm thick. It is advantageous to use thinner neoprene here as it is more elastic, seals better to the wearer's ears and is easier to hear through than a thicker amount. The strap 18 covers the wearer's ears E so as to reduce contact with the wind and water and to keep the ears warmer for those who have sensitive ears, or are prone to "surfer's ear" (exostosis), and to thereby minimize exposure to infectious diseases in the water. The strap 18 further can hold earplugs in place while the wearer is submerged.

The second blank 38 particularly has opposite end portions 40 attached at opposite end edges 40A along inner opposite portions 42 of an upper edge 44 of the band 12 defining the opening 14 therein. The opposite end portions 40 of the second blank 38 are tapered from a maximum width at the opposite end edges 40A thereof for covering the ears of the wearer to a minimum width at a middle portion 46 for extending under the chin of the wearer. The opposite end edges 40A of the second blank 38 are preferably attached to the inner opposite portions 42 of the the upper edge 44 of the band 12 so as not to interfere with the bill 16 in the ear areas. This interior location of attachment of the opposite end edges 40A to the inner opposite portions 42 enables the bill 16 to provide more shade when the sun is at one side rather than directly ahead of the wearer.

Alternatively, the opposite end edges 40A of the second blank 38 may be attached to outer opposite portions 48 of a lower edge 50 of the band 12. This location of attachment would cause the bill 16 to lie flat against the wearer's head in the ear areas and thereby provide less shade at the sides of the wearer's head.

The opposite end edges 40A of the opposite end portions 40 of the second blank 38 are preferably stitched to and can also or alternatively be glued to the opposite portions 42 or 48 of the upper or lower edges 44 or 50 of the band 12. The rear edge portions 22 of the first blank 20 are preferably glued together or alternatively stitched to one another. Preferably, the band 12 and strap 18 are fabricated having different sizes to fit different size heads. Alternatively, other releasable fastening elements such as snaps or buckles or patches 52 of complementary hook and loop fastening elements (shown in dashed outline form) can be located at rear edge portions 22 of the first blank 20 and at opposite end edges 40A of the second blank 38 and at opposite portions 42 or 48 of the upper or lower edges 44 or 50 of the band 12 to provide for adjustment of both the band 12 and the strap 18 to fit different size heads.

It should be readily apparent that the first and second blanks 20, 38 can be readily and easily produced by conventional fabrication techniques. Also, it is readily apparent that the sun visor headgear 10 can be constructed in a straightforward, simple and economical fashion from the first and second blanks 20, 38.

Figure 9:
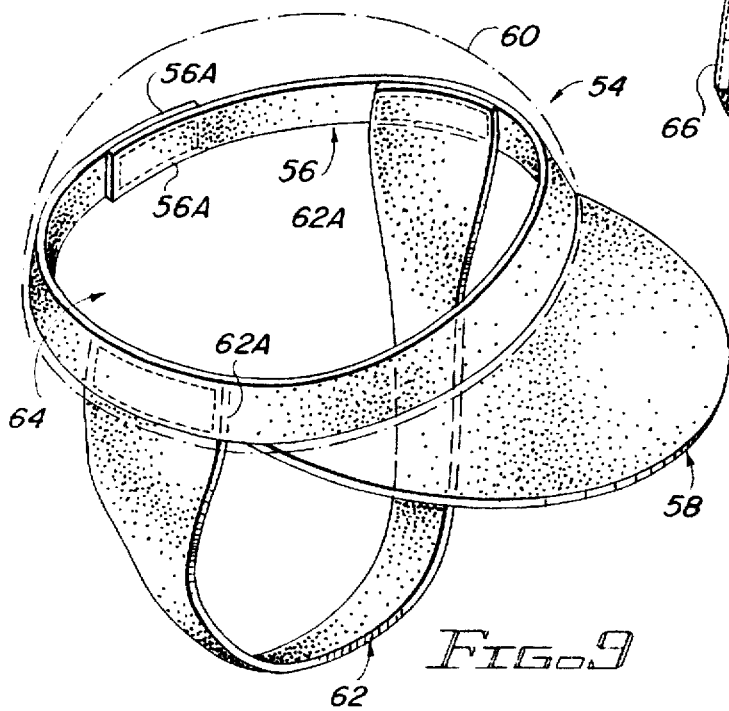
FIG. 9 is perspective view of one structural attachment of the bill, band and chin strap of the headgear of FIG. 8 to one another.
Figure 11:
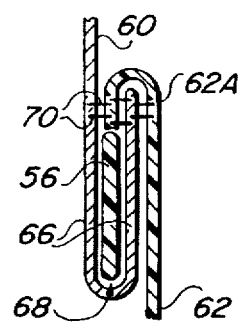
FIG. 11 is sectional view taken along line 11—11 of FIG. 8 showing another structural attachment of the bill, band, chin strap and cap piece to one another.

Referring to FIGS. 8-13, there is illustrated another embodiment of the present invention in the form of a combined sun visor and cap headgear, generally designated 54. The combined headgear 54, which except for the differences described below is generally similar to the embodiment shown in FIG. 4, also is adapted for use particularly, although not solely, during water activities to protect a wearer's face from harmful sun rays and wearer's ears from harmful wind and water. The headgear 54 basically includes an elongated band 56, a front bill 58, a cap piece 60, and a chin strap 62. The band 56 fits continuously around and surrounds the head of a wearer and defines an opening 64 therethrough for receiving the top of the head of the wearer. The front bill 58, which is made from a piece of material separate from that of the band 56, is connected to a front portion of the band 56 and extends outwardly and downwardly therefrom for shielding the face of the wearer. The cap piece 60, which is dome-shaped, is attached to the band 56 to enclose the opening 64 therein and thus to cover the head of the wearer. The chin strap 62, which is made from a piece of material separate from that of the band 56 and front bill 58, is attached either to the opposite side portions of the band 56, as seen in FIG. 9 or to the opposite side portions of the cap piece 60, as seen in FIG. 11, both located rearwardly of the opposite ends of the front bill 58. The chin strap 62 defines a loop which extends over the ears and under the chin of the wearer.

As mentioned above, the band 56 and the front bill 58 are respectively fabricated from separate first and second blanks of material which are then attached together in any suitable manner, such as by the use of a suitable adhesive. Preferably, the first and second blanks are made of substantially uniform elastic bendable material, such as neoprene. It is desirable to use a relatively thin piece of material to form the first blank defining the band 56, while a thicker piece of material is desirable to form the second blank defining the bill 58 in order for the bill not to droop. Also, the first blank defining the band 56 is now made of a substantially linear strip of material and has a pair of rear end portions 56A which are the only location at which the first blank is either fixedly, or alternatively releasably and adjustably in any well-known manner, attached to itself to form the band 56.

The cap piece 60 preferably is made of a flexible thin material which is substantially water repellent so that it does not absorb water and become water-logged and heavy. Also, by way of example only, the cap piece 60 can have a lower edge portion 66 which is folded back on itself and then secured to itself along the interior of the cap piece 60 so as to define an enclosed channel 68 through the folded lower edge portion 66. The elongated band 56 is received through the enclosed channel 68. As seen in the construction shown in FIG. 11, the opposite ends 62A of the chin strap 62 are attached, such as by being stitched at 70, to opposite side portions of the folded lower edge portion 66 of the cap piece 60 rearwardly of the opposite ends of the front bill 58.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

We claim:

1. A sun visor and cap headgear, comprising:
   (a) a band for fitting continuously around and surrounding the head of a wearer and defining an opening therethrough for receiving the top of the head of a wearer;
   (b) a front bill connected to said band and extending outwardly and downwardly therefrom for shielding the face of a wearer;
   (c) a cap piece attached to said band to enclose said opening therein and to cover the head of a wearer; and
   (d) a chin strap attached to one of the opposite side portions of said cap piece and opposite side portions of said band rearwardly of said front bill and defining a loop therebetween for extending over the ears and under the chin of a wearer;

(e) wherein said band and said bill are respectively fabricated of different first and second blanks of material being attached together, said first and second blanks of said band and front bill being made of a substantially uniform elastic bendable material.

2. The headgear of claim 1 wherein said first blank defining said band has a pair of rear edge portions defining the only location at which said first blank is attached to itself to form said band.

3. The headgear of claim 1 wherein opposite ends of said chin strap are attached along said opposite side portions of said cap piece.

4. A sun visor and cap headgear, comprising:

(a) a band for fitting continuously around and surrounding the head of a wearer and defining an opening therethrough for receiving the top of the head of a wearer;

(b) a front bill connected to said band and extending outwardly and downwardly therefrom for shielding the face of a wearer;

(c) a cap piece attached to said band to enclose said opening therein and to cover the head of a wearer; and (d) a chin strap attached to one of the opposite side portions of said cap piece and opposite side portions of said band rearwardly of said front bill and defining a loop therebetween for extending over the ears and under the chin of a wearer;

(e) wherein said chin strap is fabricated from a blank of material having a bow tie shaped configuration.

5. The headgear of claim 4 wherein opposite ends of said chin strap are attached along said opposite side portions of said cap piece.

6. A sun visor and cap headgear, comprising:

(a) a band for fitting continuously around and surrounding the head of a wearer and defining an opening therethrough for receiving the top of the head of a wearer;

(b) a front bill connected to said band and extending outwardly and downwardly therefrom for shielding the face of a wearer;

(c) a cap piece attached to said band to enclose said opening therein and to cover the head of a wearer; and (d) a chin strap attached to one of the opposite side portions of said cap piece and opposite side portions of said band rearwardly of said front bill and defining a loop therebetween for extending over the ears and under the chin of a wearer;

(e) wherein opposite ends of said chin strap are attached along said opposite side portions of said cap piece;

(f) wherein said chin strap is fabricated from a blank of material having opposite end portions attached along opposite side portions of said cap piece and tapered from a maximum width at opposite end edges of said blank for covering the ears of a wearer to a minimum width at a middle portion of said blank for extending under the chin of a wearer.

7. A sun visor and cap headgear, comprising:

(a) a band for fitting continuously around and surrounding the head of a wearer and defining an opening therethrough for receiving the top of the head of a wearer;

(b) a front bill connected to said band and extending outwardly and downwardly therefrom for shielding the face of a wearer;

(c) a cap piece attached to said band to enclose said opening therein and to cover the head of a wearer; and (d) a chin strap attached to one of the opposite side portions of said cap piece and opposite side portions of said band rearwardly of said front bill and defining a loop therebetween for extending over the ears and under the chin of a wearer;

(e) wherein said cap piece has a lower edge portion folded and secured back on itself along the interior of said cap piece so as to define an enclosed channel through said folded lower edge portion of said cap piece receiving said band.

8. The headgear of claim 7 wherein opposite ends of said chin strap are attached to opposite side portions of said lower edge portion of said cap piece.

* * * * *